(12) United States Patent
Hossainy et al.

(10) Patent No.: US 7,396,539 B1
(45) Date of Patent: Jul. 8, 2008

(54) STENT COATINGS WITH ENGINEERED DRUG RELEASE RATE

(75) Inventors: Syed F A. Hossainy, Fremont, CA (US); Gordon Stewart, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1035 days.

(21) Appl. No.: 10/177,154

(22) Filed: Jun. 21, 2002

(51) Int. Cl.
*A61F 2/00* (2006.01)
(52) U.S. Cl. ..................................... 424/423
(58) Field of Classification Search .................. 424/423
See application file for complete search history.

(56) References Cited

U.S. PATENT DOCUMENTS

| | | | |
|---|---|---|---|
| 2,968,649 A | 1/1961 | Pailthorp et al. | |
| 3,051,677 A | 8/1962 | Rexford | |
| 3,178,399 A | 4/1965 | Lo | |
| 3,324,069 A | 6/1967 | Koblitz et al. | |
| 3,779,805 A | 12/1973 | Alsberg | |
| 3,856,827 A | 12/1974 | Cavitt | |
| 4,076,929 A | 2/1978 | Dohany | |
| 4,197,380 A | 4/1980 | Chao et al. | |
| 4,304,010 A | 12/1981 | Mano | |
| 4,346,710 A | 8/1982 | Thanawalla et al. | |
| 4,353,960 A | 10/1982 | Endo et al. | |
| 4,399,264 A | 8/1983 | Squire | |
| 4,413,359 A | 11/1983 | Akiyama et al. | |
| 4,423,183 A | 12/1983 | Close | |
| 4,485,250 A | 11/1984 | Squire | |
| 4,530,569 A | 7/1985 | Squire | |
| 4,564,013 A | 1/1986 | Lilenfeld et al. | |
| 4,569,978 A | 2/1986 | Barber | |
| 4,632,842 A | 12/1986 | Karwoski et al. | |
| 4,636,346 A | 1/1987 | Gold et al. | |
| 4,718,907 A | 1/1988 | Karwoski et al. | |
| 4,733,665 A | 3/1988 | Palmaz | |
| 4,749,585 A | 6/1988 | Greco et al. | |
| 4,754,009 A | 6/1988 | Squire | |
| 4,770,939 A | 9/1988 | Sietsess et al. | |
| 4,800,882 A | 1/1989 | Gianturco | |
| 4,871,357 A | 10/1989 | Hsu et al. | |
| 4,876,109 A | 10/1989 | Mayer et al. | |
| 4,886,062 A | 12/1989 | Wiktor | |
| 4,897,457 A | 1/1990 | Nakamura et al. | |
| 4,908,404 A | 3/1990 | Benedict et al. | |
| 4,910,276 A | 3/1990 | Nakamura et al. | |
| 4,931,287 A | 6/1990 | Bae et al. | 424/484 |
| 4,935,477 A | 6/1990 | Squire | |
| 4,948,851 A | 8/1990 | Squire | |
| 4,973,142 A | 11/1990 | Squire | |
| 4,975,505 A | 12/1990 | Squire | |
| 4,977,008 A | 12/1990 | Squire | |
| 4,977,025 A | 12/1990 | Squire | |
| 4,977,026 A | 12/1990 | Squire | |
| 4,977,297 A | 12/1990 | Squire | |
| 4,977,901 A | 12/1990 | Ofstead | 128/772 |
| 4,982,056 A | 1/1991 | Squire | |
| 4,985,308 A | 1/1991 | Squire | |
| 4,999,248 A | 3/1991 | Squire | |
| 5,000,547 A | 3/1991 | Squire | |
| 5,006,382 A | 4/1991 | Squire | |
| 5,030,394 A | 7/1991 | Sietses et al. | |
| 5,047,020 A | 9/1991 | Hsu | |
| 5,051,114 A | 9/1991 | Nemser et al. | |
| 5,051,978 A | 9/1991 | Mayer et al. | |
| 5,053,048 A | 10/1991 | Pinchuk | |
| 5,076,659 A | 12/1991 | Bekiarian et al. | |
| 5,093,427 A | 3/1992 | Barber | |
| 5,107,852 A | 4/1992 | Davidson et al. | |
| 5,110,645 A | 5/1992 | Matsumoto et al. | |
| 5,112,457 A | 5/1992 | Marchant | 204/165 |
| 5,176,972 A | 1/1993 | Bloom et al. | |
| 5,185,408 A | 2/1993 | Tang et al. | |
| 5,246,451 A | 9/1993 | Trescony et al. | |
| 5,276,121 A | 1/1994 | Resnick | |
| 5,296,283 A | 3/1994 | Froggatt | |
| 5,302,385 A | 4/1994 | Khan et al. | |
| 5,308,685 A | 5/1994 | Froggatt | |
| 5,310,838 A | 5/1994 | Hung et al. | |
| 5,324,889 A | 6/1994 | Resnick | |
| 5,326,839 A | 7/1994 | Resnick | |
| 5,328,471 A | 7/1994 | Slepian | 604/101 |
| 5,336,518 A | 8/1994 | Narayanan et al. | |
| 5,338,608 A | 8/1994 | Resnick | |
| 5,342,348 A | 8/1994 | Kaplan | |

(Continued)

FOREIGN PATENT DOCUMENTS

DE 19723723 A1 12/1998

(Continued)

OTHER PUBLICATIONS

U.S. Appl. No. 09/966,036, filed Sep. 28, 2001, Happ.

(Continued)

*Primary Examiner*—Sharon E. Kennedy
(74) *Attorney, Agent, or Firm*—Squire Sanders & Dempsey, LLP

(57) ABSTRACT

Coatings and methods of forming coatings for implantable medical devices, such as stents, are described. The coatings are used for the sustained release of a therapeutic agent or drug.

18 Claims, 4 Drawing Sheets

U.S. PATENT DOCUMENTS

| | | | |
|---|---|---|---|
| 5,353,368 A | 10/1994 | Resnick | |
| 5,354,910 A | 10/1994 | Hung et al. | |
| 5,368,566 A | 11/1994 | Crocker | |
| 5,380,299 A | 1/1995 | Fearnot et al. | |
| 5,383,853 A | 1/1995 | Jung et al. | |
| 5,383,928 A | 1/1995 | Scott et al. | |
| 5,395,311 A | 3/1995 | Andrews | |
| 5,403,341 A | 4/1995 | Solar | |
| 5,408,020 A | 4/1995 | Hung et al. | |
| 5,417,969 A | 5/1995 | Hsu et al. | |
| 5,443,458 A | 8/1995 | Eury | |
| 5,447,724 A | 9/1995 | Helmus et al. | |
| 5,455,040 A | 10/1995 | Marchant | 424/426 |
| 5,464,650 A | 11/1995 | Berg et al. | 427/2.3 |
| 5,545,208 A | 8/1996 | Wolff et al. | |
| 5,560,463 A | 10/1996 | Link et al. | |
| 5,562,734 A | 10/1996 | King | |
| 5,569,463 A | 10/1996 | Helmus et al. | |
| 5,575,818 A | 11/1996 | Pinchuk | |
| 5,578,073 A | 11/1996 | Haimovich et al. | 623/1 |
| 5,584,877 A | 12/1996 | Miyake et al. | 623/1 |
| 5,591,224 A | 1/1997 | Schwartz et al. | |
| 5,604,283 A | 2/1997 | Wada et al. | |
| 5,605,696 A | 2/1997 | Eury et al. | 424/423 |
| 5,616,608 A | 4/1997 | Kinsella et al. | |
| 5,628,728 A | 5/1997 | Tachibana et al. | |
| 5,632,771 A | 5/1997 | Boatman et al. | |
| 5,632,776 A | 5/1997 | Kurumatani et al. | |
| 5,632,840 A | 5/1997 | Campbell | |
| 5,635,201 A | 6/1997 | Fabo | |
| 5,667,767 A | 9/1997 | Greff et al. | 424/9.411 |
| 5,670,558 A | 9/1997 | Onishi et al. | 523/112 |
| 5,679,400 A | 10/1997 | Tuch | |
| 5,684,061 A | 11/1997 | Ohnishi et al. | |
| 5,691,311 A | 11/1997 | Maraganore et al. | |
| 5,697,967 A | 12/1997 | Dinh et al. | |
| 5,700,286 A | 12/1997 | Tartaglia et al. | 623/1 |
| 5,713,949 A | 2/1998 | Jayaraman | |
| 5,716,981 A | 2/1998 | Hunter et al. | 514/449 |
| 5,750,234 A | 5/1998 | Johnson et al. | |
| 5,758,205 A | 5/1998 | Hara et al. | |
| 5,759,205 A | 6/1998 | Valentini | 623/16 |
| 5,760,118 A | 6/1998 | Sinclair et al. | |
| 5,776,184 A | 7/1998 | Tuch | |
| 5,804,318 A | 9/1998 | Pinchuk et al. | |
| 5,820,917 A | 10/1998 | Tuch | |
| 5,824,048 A | 10/1998 | Tuch | |
| 5,824,049 A | 10/1998 | Ragheb et al. | 623/1 |
| 5,827,587 A | 10/1998 | Fukushi | |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,858,990 A | 1/1999 | Walsh | 514/44 |
| 5,860,963 A | 1/1999 | Azam et al. | |
| 5,861,168 A | 1/1999 | Cooke et al. | |
| 5,865,814 A | 2/1999 | Tuch | 604/265 |
| 5,869,127 A | 2/1999 | Zhong | |
| 5,873,904 A | 2/1999 | Ragheb et al. | 623/1 |
| 5,874,165 A | 2/1999 | Drumheller | |
| 5,879,697 A | 3/1999 | Ding et al. | |
| 5,897,911 A | 4/1999 | Loeffer | |
| 5,900,425 A | 5/1999 | Kanikanti et al. | |
| 5,911,704 A | 6/1999 | Humes | |
| 5,921,933 A | 7/1999 | Sarkis et al. | |
| 5,922,393 A | 7/1999 | Jayaraman | |
| 5,928,279 A | 7/1999 | Shannon et al. | |
| 5,932,299 A | 8/1999 | Katoot | |
| 5,945,115 A | 8/1999 | Dunn et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,015,541 A | 1/2000 | Greff et al. | 424/1.25 |
| 6,033,724 A | 3/2000 | Molitor | |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,534 A | 5/2000 | Ronan et al. | |
| 6,080,488 A | 6/2000 | Hostettler et al. | 428/423.3 |
| 6,090,134 A | 7/2000 | Tu et al. | |
| 6,096,070 A | 8/2000 | Ragheb et al. | 623/1 |
| 6,096,396 A | 8/2000 | Patton et al. | |
| 6,096,798 A | 8/2000 | Luthra et al. | |
| 6,096,809 A | 8/2000 | Lorcks et al. | |
| 6,099,562 A | 8/2000 | Ding et al. | 623/1.46 |
| 6,099,563 A | 8/2000 | Zhong | |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,124,045 A | 9/2000 | Soda et al. | |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,179,817 B1 | 1/2001 | Zhong | |
| 6,197,051 B1 | 3/2001 | Zhong | |
| 6,203,551 B1 | 3/2001 | Wu | 606/108 |
| 6,214,901 B1 | 4/2001 | Chudzik et al. | 523/113 |
| 6,224,894 B1 | 5/2001 | Jamiolkowski et al. | 424/426 |
| 6,231,590 B1 | 5/2001 | Slaikeu et al. | 606/200 |
| 6,242,041 B1 | 6/2001 | Katoot et al. | 427/2.24 |
| 6,254,632 B1 | 7/2001 | Wu et al. | 623/1.15 |
| 6,258,121 B1 | 7/2001 | Yang et al. | 623/1.46 |
| 6,262,034 B1 | 7/2001 | Mathiowitz et al. | 514/44 |
| 6,273,913 B1 | 8/2001 | Wright et al. | 623/1.42 |
| 6,299,604 B1 | 10/2001 | Ragheb et al. | |
| 6,319,520 B1 | 11/2001 | Wuthrich et al. | 424/482 |
| 6,344,035 B1 | 2/2002 | Chudzik et al. | 604/265 |
| 6,362,271 B1 | 3/2002 | Lin et al. | |
| 6,408,878 B2 | 6/2002 | Unger et al. | |
| 6,410,612 B1 | 6/2002 | Hatanaka | |
| 6,464,683 B1 | 10/2002 | Samuelson et al. | |
| 6,503,556 B2 | 1/2003 | Harish et al. | |
| 6,545,097 B2 | 4/2003 | Pinchuk et al. | |
| 6,551,708 B2 | 4/2003 | Tsuda et al. | |
| 6,716,444 B1 | 4/2004 | Castro et al. | |
| 6,746,773 B2 | 6/2004 | Llanos et al. | |
| 6,824,559 B2 * | 11/2004 | Michal | 623/1.15 |
| 2001/0014717 A1 | 8/2001 | Hossainy et al. | 525/60 |
| 2001/0029351 A1 | 10/2001 | Falotico et al. | |
| 2002/0051730 A1 | 5/2002 | Bodnar et al. | |
| 2002/0090389 A1 | 7/2002 | Humes et al. | |
| 2002/0094440 A1 | 7/2002 | Lianos et al. | 428/421 |
| 2002/0099438 A1 | 7/2002 | Furst | |
| 2002/0111590 A1 | 8/2002 | Davila et al. | 604/265 |
| 2002/0122877 A1 | 9/2002 | Harish et al. | |
| 2002/0123801 A1 | 9/2002 | Pacetti et al. | |
| 2002/0133183 A1 | 9/2002 | Lentz et al. | |
| 2002/0143386 A1 | 10/2002 | Davila et al. | |
| 2002/0165608 A1 | 11/2002 | Llanos et al. | |
| 2002/0188037 A1 | 12/2002 | Chudzik et al. | |
| 2003/0004563 A1 | 1/2003 | Jackson et al. | |
| 2003/0031780 A1 | 2/2003 | Chudzik et al. | |
| 2003/0039689 A1 | 2/2003 | Chen et al. | |
| 2003/0060877 A1 | 3/2003 | Falotico et al. | |
| 2003/0065346 A1 | 4/2003 | Evens et al. | |
| 2003/0065377 A1 | 4/2003 | Davila et al. | |
| 2003/0073961 A1 | 4/2003 | Happ | |
| 2003/0077312 A1 | 4/2003 | Schmulewicz et al. | |
| 2004/0063805 A1 | 4/2004 | Pacetti et al. | |

| | | |
|---|---|---|
| 2004/0102758 A1 | 5/2004 | Davila et al. |

FOREIGN PATENT DOCUMENTS

| | | |
|---|---|---|
| EP | 0568310 A1 | 11/1993 |
| EP | 0623354 A1 | 11/1994 |
| EP | 0633032 A1 | 1/1995 |
| EP | 0 665 023 | 8/1995 |
| EP | 0747069 A2 | 12/1996 |
| EP | 0815803 A1 | 1/1998 |
| EP | 0893108 A2 | 1/1999 |
| EP | 0950385 A2 | 10/1999 |
| EP | 0950386 A2 | 10/1999 |
| EP | 0 970 711 | 1/2000 |
| EP | 0968688 A1 | 1/2000 |
| EP | 0997115 A2 | 5/2000 |
| EP | 1 023 879 | 8/2000 |
| EP | 1 192 957 | 4/2002 |
| WO | WO 92/05695 | 4/1992 |
| WO | WO 92/18320 | 10/1992 |
| WO | WO 94/02185 | 2/1994 |
| WO | WO 96/21404 | 7/1996 |
| WO | WO 97/41164 | 11/1997 |
| WO | WO 98/08463 | 3/1998 |
| WO | WO 98/13405 | 4/1998 |
| WO | WO 98/36784 | 8/1998 |
| WO | WO 98/58680 | 12/1998 |
| WO | WO 99/32051 | 7/1999 |
| WO | WO 99/55396 | 11/1999 |
| WO | WO 00/02599 | 1/2000 |
| WO | WO 00/12147 | 3/2000 |
| WO | WO 00/27455 | 5/2000 |
| WO | WO 00/29043 | 5/2000 |
| WO | WO 00/32255 | 6/2000 |
| WO | WO 00/38754 | 7/2000 |
| WO | WO 00/41738 | 7/2000 |
| WO | WO 00/64506 | 11/2000 |
| WO | WO 01/01890 | 1/2001 |
| WO | WO 01/30403 A1 | 5/2001 |
| WO | WO 01/49340 | 7/2001 |
| WO | WO 01/87342 A2 | 11/2001 |
| WO | WO 01/87368 | 11/2001 |
| WO | WO 01/87372 | 11/2001 |
| WO | WO 01/87376 A1 | 11/2001 |
| WO | WO 02/24249 | 3/2002 |
| WO | WO 02/26139 A1 | 4/2002 |
| WO | WO 02/26271 A | 4/2002 |
| WO | WO 02/26281 A1 | 4/2002 |
| WO | WO 02/34311 | 5/2002 |
| WO | WO 02/47731 | 6/2002 |
| WO | WO 02/47732 | 6/2002 |
| WO | WO 03/022324 | 3/2003 |

OTHER PUBLICATIONS

Anonymous, *Rolling Therapeutic Agent Loading Device for Therapeutic Agent Delivery of Coated Stent*, Research Disclosure, Publ., Hampshire, GB, No. 434, p. 975 (2000).
Arnold et al., *Effects of environment on the creep properties of a poly (ethylmethacrylate) based bone cement* J. Mater. Sci: Mater. In Med., vol. 12, pp. 707-717 (2001).
Bellex International, CYTOP®, *Amorphous Fluorocarbon Polymer*, 1 page (no date).
Bellex International, *Selected CYTOP Physical Data*, 1 page (no date).
Bellex International, *CYTOP®*, http://www.bellexinternational.com/cytop.htm, printed Mar. 30, 2001, 1 page.
Cifková et al., *Irritation effects of residual products derived from p(HEMA) gels*, Biomaterials, vol. 9, (Jul. 1998), pp. 372-375.
Dalsin et al., *DOPA: A New Anchor for PEGylation of Biomaterial Surfaces*, Soc. For Biomaterials 28th Annual Meeting Transactions, pp. 40 (2002).

Deb et al., *Effect of crosslinking agents on poly(ethylmethacrylate) bone cements*, J. of Mater.Sci: Mater. In Med., vol. 8, pp. 829-833 (1997).
Del Guerra et al., *In vitro biocompatibility of fluorinated polyurethanes*, J. Mater. Sci. in Med., vol. 5, pp. 452-456 (1994).
DuPont, *Teflon AF 1601S amorphous fluoropolymer solutions*, product information, 2 pages (1998).
DuPont, *Processing of Teflon® AF*, Teflon Amorphous Fluoropolymer, http://www.dupont.com/teflon/af/processing.html, printed Mar. 30, 2001, 1 page.
DuPont, *High-Performance/Potential Applications*, Teflon Amorphous Fluoropolymer, http://www.dupont.com/teflon/af/potapps.html, printed Mar. 30, 2001, 3 pages.
DuPont, *Performance Comparison of Teflon AF*, Teflon Amorphous Fluoropolymer, http://www.dupont.com/teflon/af/performance.html, printed Mar. 30, 2001, 3 pages.
DuPont, *Unique Properties of Teflon® AF*, Teflon Amorphous Fluoropolymer, http://www.dupont.com/teflon/af/unique.html, printed Mar. 30, 2001, 3 pages.
DuPont, *Teflon® RF: A New Generation of High-Performance Fluoropolymer Resins*, http://www.dupont.com/teflon/af/index.html, printed Mar. 30, 2001, 1 page.
DuPont, *Teflon® Protects Superconductors Against Acid*, Teflon Amorphous Fluoropolymer, http://www.dupont.com/teflon/af/superconductor.html, printed Sep. 21, 2004, 2 pages.
DuPont, *Available Grades of DuPont Teflon® AF*, Teflon Amorphous Fluoropolymer, http://www.dupont.com/teflon/af/grades.html, printed Sep. 21, 2004, 2 pages.
DuPont, *Teflon® AF amorphous fluoropolymers*, Product Information, 6 pages (1998).
DuPont, Sales Notice, Teflon Amorphous Fluoropolymer, http://www.dupont.com/teflon/af/patent.html, printed Sep. 21, 2004, 2 pages.
Fine et al., *Improved nerve regeneration through piezoelectric vinylidenefluoride- trifluoroethylene copolymer guidance channels*, Biomaterials, vol. 12, October, pp. 775-780 (1991).
Fischell, *Polymer Coatings for Stents*, Circulation, 94:1494-95 (1996).
Gullickson, *Reference Data Sheet on Common Chlorinated Solvents*, http://www.mcs.net/~hutter/tee/chlorina.html, printed Mar. 30, 2001, 5 pages.
Gunn et al., *Stent coatings and local drug delivery*, Eur. Heart J., vol. 20, issue 23, pp. 1693-1700 (1999).
Harper et al., *Fatique Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.
Harper et al., *Mechanical properties of hydroxyapatite reinforced poly (ethyl methacrylate) bone cement after immersion in a physiological solution: influence of a silane coupling agent*, J. Mater. Sci.: Mater. In Med., vol. 11, pp. 491-497 (2000).
Kruft et al., *Studies on radio-opaque polymeric biomaterials with potential applications to endovascular prostheses*, Biomaterials, vol. 17, No. 18, pp. 1803-1812 (1996).
Lambert et al., *Localized Arterial Wall Drug Delivery From a Polymer-Coated Removable Metallic Stent*, Circulation, vol. 90, No. 2, pp. 1003-1011 (1994).
Laroche et al., *Polyvinylidene fluoride (PVDF) as a biomaterial: From polymeric raw material to monofilament vascular suture*, J. of Biomedical Mat. Research, vol. 29, pp. 1525-1536 (1995).
Lin et al., *Fluropolymer Alloys Performance Optimization of PVDF Alloys*, Fluoropolymers 2 Properties, edited by Hougham et al., Plenum Publishers N.Y. pp. 121-136 (1999).
Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).
Luthra, *Biointeractions Ltd (BIL)*, http://www.biomateria.com/biointeractions.html, printed Sep. 21, 2004, 3 pages.
3M, *Specialty Fluids 3M™ Fluorinert™ Liquids, Typical Properties*, http://www.3m.com/market/industrial/fluids/fluoprop.html, printed Mar. 30, 2001, 3 pages.
Materials Engineering, *Applications in Design/Manufacturing/R &D*, Materials Selector 1993, Penton Publishing (1992) 6 pgs.

Medtronic, Trillium Affinity NT, Oxygenator, Product Information, 6 pages (2000).

NCMS SOLV-DB, *Query Results for: CFC*, http://solvdb.ncms.org/CAT01.idc?chemcat=CFC, printed Mar. 30, 2001, 2 pages.

NCMS SOLV-DB, *Query Results for: FC-75 Fluorinert*, http://solvdb.ncms.org/common01.idc, printed Mar. 30, 2001, 2 pages.

Novick et al., *Protein-containing hydrophobic coatings and films*, Biomaterials, vol. 23, No. 2 (2002) pp. 441-448.

Parkell, Inc., *Snap Powder-Liquid Temporary Crown and Bridge Resin*, http://www.parkell.com/snap.html, printed Oct. 21, 2004, 1 pg.

Parkell, Inc., *Material Safety Data Sheets*, http://www.parkell.com/msds.html, printed Oct. 21, 2004, 2 pgs.

Parkell, Inc., *MSDS No. S426, VAR, Material Safety Data Sheet*, 2 pgs (2002).

Parkell, Inc., MSDS No. S441, Material Safety Data Sheet, 2 pgs (2002).

Porté-Durrieu et al., *Surface Treatment of Biomaterials by Gamma and Swift Heavy Ions Grafting*, Nuclear Instruments and Methods in Physics Research, vol. B 151, pp. 404-415 (1999).

Porté-Durrieu et al., *Development of "Heparin-Like" Polymers Using Swift Heavy Ion and Gamma Radiation. I. Preparation and Characterization of the Materials*, Surface Treatment of Biomaterials, pp. 119-127 (2000).

Revell et al., *Experimental Studies of the Biological Response to a New Bone Cement: II Soft Tissue Reactions in the Rat*, Clinical Materials, vol. 10, pp. 233-238 (1992).

Techspray, Bulk Solvents, http://www.techspray.com/bulksup.htm, printed Sep. 21, 2004, 3 pages.

Techspray, *Flux Remover AMS*, Product Information, http://www.techspray.com/1665info.htm, printed Aug. 28, 2001, 2 pages.

Teomin et al., *Perivascular delivery of heparin for the reduction of smooth muscle cell proliferation after endothelial injury*, J. of Controlled Release, vol. 60, pp. 129-142 (1999).

Topol et al., *Frontiers in Interventional Cardiology*, Circulation, vol. 98, pp. 1802-1820 (1998).

Urban et al., *Why Make Monofilament Sutures Out of Polyvinylidene Fluoride?*, ASAIO J., vol. 40, No. 2, pp. 145-156 (1994).

Verweire et al., *Evaluation of fluorinated polymers as coronary stent coating*, J. Mater.Sci: Mater. In Med., vol. 11, No. 4, pp. 207-212 (2000).

Weightman et al., *The Mechanical Properties of Cement and Loosening of the Femoral Component of Hip Replacements*, J. Bone and Joint Surg., vol. 69-B, No. 4, pp. 558-564 (Aug. 1987).

Wholey et al., *Global Experience in Cervical Carotid Artery Stent Placement*, Catherization and Cardiovascular Interventions, vol. 50, No. 2, pp. 160-167 (2000).

Woo et al., *Phase Behavior of Polycarbonate Blends with Selected Halogenated Polymers*, J. Appl. Polym. Sci., vol. 30, pp. 4243-4249 (1985).

U.S. Appl. No. 09/894,293, filed Jun. 27, 2001, Roorda et al.

European Search Report for 03 738 920.2-2107, mailed Sep. 5, 2007, 7 pgs.

\* cited by examiner

STENT COATINGS WITH ENGINEERED DRUG RELEASE RATE

BACKGROUND OF THE INVENTION

1. Field of the Invention

This invention relates to implantable medical devices such as stents. More particularly, the invention relates to coatings for stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

The current state of the art discloses a variety of polymeric material that can be used for the sustained delivery of therapeutic substances. What is lacking, however, is coating configurations and layering designs which provide for tailored drug delivery capabilities. The embodiments of the invention provide for improved coating patterns for stents or other implantable medical devices.

SUMMARY

In accordance with one embodiment, a stent having a coating is provided. The coating comprises a first region including a thermoplastic polyacrylate material and a therapeutic substance and a second region free from any therapeutic substances disposed on the surface of the stent and beneath the first region. The thermoplastic polyacrylate material can comprise oligomers, pre-polymers, homopolymers, copolymers, or terpolymers of alkylacrylates or alkylmethacrylates. In one embodiment, the polyacrylate material is poly(n-butyl methacrylate). The second region can include a non-acrylate polymer, such as an ethylene vinyl alcohol copolymer. In one embodiment, the coating can include a third region disposed over the first region, the third region including a thermoplastic polyacrylate material and optionally a therapeutic substance. The first region can have a variable thickness along at least a segment of the length of the stent such that the concentration of the substance varies along the length of the stent.

In accordance with another embodiment of the invention, a stent is provided comprising a coating, wherein the coating includes a first, second, and third layers disposed over one another wherein at least two of the layers include a thermoplastic polyacrylate material and wherein at least one of the layers includes a therapeutic substance. In one embodiment, the first layer is disposed on the outer surface of the stent, the second and third layers include the thermoplastic polyacrylate material, and the therapeutic substance is contained in the second layer and optionally the third layer but not the first layer. In accordance with another embodiment, the first layer and the third layer include the therapeutic substance but not the second layer and the second layer and the third layer include the thermoplastic polyacrylate material. In accordance with yet another embodiment, the first, second and third layers include the thermoplastic polyacrylate material and at least one of the layers is free from any therapeutic substances.

A stent comprising a coating having a variable thickness along at least a portion of the length of the stent is also provided so as to provide a concentration gradient of an active agent or agents along from a thin region of the coating to a thicker region of the coating.

In accordance with yet another embodiment, a method of coating a stent is provided, the method comprises forming a coating on the stent, the coating including a first region having a thermoplastic polyacrylate material and a therapeutic substance and a second region free from any therapeutic substances disposed on the surface of the stent beneath the first region.

In accordance with yet another embodiment of the invention, a method of coating a stent is provided comprising forming at least three layers of coating on a stent, wherein at least two of the layers include a thermoplastic polyacrylate material and wherein at least one of the layers includes a therapeutic substance.

In accordance with yet another embodiment of the invention, a method of coating a stent is provided comprising depositing a coating on the stent wherein the coating has a variable thickness along at least a segment of the length of the stent.

In accordance with yet another embodiment of the invention, a method of coating a stent, is provided comprising, depositing a first layer on the stent, the first layer including a first therapeutic substance; masking a region of the first layer; depositing a second layer on the first layer not covered by the masking layer, the second layer including a second therapeutic substance.

DETAILED DESCRIPTION

Figure 1A:
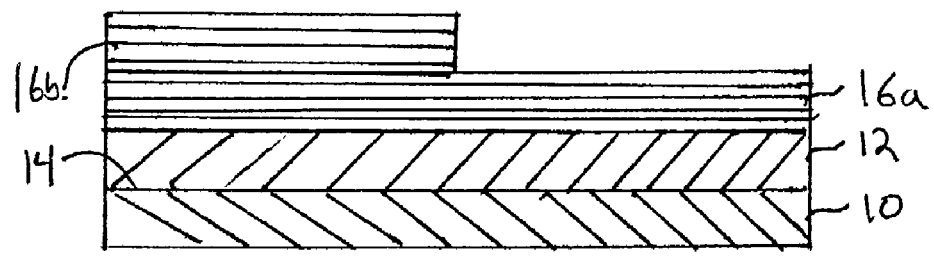
FIGS. 1A, 1B, and 1C illustrate a process for fabricating a stent coating according to one embodiment of the present invention.

A stent coating having an engineered drug release rate can be fabricated by depositing on the stent any combination of the following layers, but for a reservoir layer which must be present in the coating: a primer layer; a reservoir layer of or containing an active agent or a drug; a topcoat layer free from any agents or drugs for serving as a rate reducing membrane; and a finishing coat layer. The finishing coat layer, which if used would be the outermost layer in the coating configuration for contacting the vessel tissues, can include an active agent or can be modified to have therapeutic materials, such as heparin, attached or conjugated to the surface thereof. Alternatively, the finishing coat layer can be made from a very bio-friendly material such a poly ethylene glycol (PEG). The purpose of the finishing coat layer is to reduce or prevent any adverse effects, such as more than acceptable degrees of inflammation or thrombi accumulation, which may be caused by the presence of the coated stent. The finishing coat layer can also serve as a rate limiting membrane for reducing the rate of release of the agent from the reservoir layer.

To deposit any of the coating layers, techniques known to those having ordinary skill in the art can be used. For example, a polymer can be dissolved in a solvent, or a mixture of solvents, and the resulting composition can be sprayed on the stent or the stent can be immersed in the composition. In one embodiment, thermoplastic polyacrylate materials can be used for any of the aforementioned layers or combination of layers. "Thermoplastic polyacrylate materials" are broadly defined as materials which include thermoplastic polyacrylates. "Polyacrylates" are defined to include oligomers, pre-polymers, homopolymers, copolymers, terpolymers, etc. of alkylacrylates or alkylmethacrylates, and blends thereof. Thermoplastic polyacrylate materials can also include blends of thermoplastic polyacrylates with non-acrylic materials.

Representative alkyl groups in alkylacrylates or alkylmethacrylates include $C_1$-$C_{12}$ straight-chained or branched alkyls. Examples of alkylacrylates or alkylmethacrylates that can be used include poly(n-butyl methacrylate) (PBMA), poly(ethyl methacrylate) (PEMA), and poly(ethyl methacrylate-co-butyl methacrylate) [P(EMA-BMA)].

Examples of suitable non-acrylic materials that can be blended with thermoplastic polyacrylates include fluorinated polymers and/or copolymers, such as poly(vinylidene fluoride) (PVDF) and poly(vinylidene fluoride-co-hexafluoro propene) (PVDF-HFP). One example of a commercially available fluorinated polymer that can be used is a PVDF resin distributed by ATOFINA Chemicals, Inc. of Philadelphia, Pa. under the trade name KYNAR. A suitable blend of a thermoplastic polyacrylate and a fluorinated polymer can contain between about 10 and about 95% mass of the fluorinated polymer. In another embodiment, the non-acrylic polymer can be poly(ethylene-co-vinyl alcohol) (also known as EVAL or EVOH). Poly(ethylene-co-vinyl alcohol) is available from Adrich Co., Milwaukee Wis. or EVAL Company of America, Lisle, Ill. These non-acrylic polymers, however, need not be used with the thermoplastic polyacrylate and can be used alone or in combination with other polymers to form any of the coating layers.

Representative examples of other polymers that can be used for any of the coating layer included poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of some solvents suitable for making the composition include N,N-dimethylacetamide (DMAC), N,N-dimethylformamide (DMF), tethrahydrofurane (THF), cyclohexanone, xylene, toluene, and acetone. Solvent mixtures can also be used as well. One representative examples of a suitable mixture is FLUX REMOVER AMS, a trade name of a solvent mixture manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance methanol, with trace amounts of nitromethane.

In on embodiment, the agent or drug can be dissolved in the composition or dispersed in the composition in fine particles for manufacturing the reservoir layer and the finishing coating layer. The agent can include any substance capable of exerting a therapeutic or prophylactic effect in the practice of the present invention. The drug may include small molecule drugs, peptides, proteins, and oligonucleotides. One example of an agent that can be used by being incorporated into the reservoir layer or the finishing coating layer is estradiol. By way of example, the mass ratio between estradiol and the polymer can be between about 5:1 and 0.2:1 for the finishing coat layer and between about 1:2 and 1:0.6 for the reservoir layer. Examples of other drugs include those that fall under the genus of antiproliferative, antineoplastic, anti-inflammatory, antiplatelet, anticoagulant, antifibrin, antithrombin, antimitotic, antibiotic, antiallergic and antioxidant substances. Specific examples include actinomycin D, paclitaxel, docetaxel, methotrexate, azathioprine, vincristine, vinblastine, fluorouracil, doxorubicin hydrochloride, mitomycin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIbIIIa platelet membrane receptor antagonist antibody, recombinant hirudin, angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin and 40-O-[2-(2-hydroxy)ethoxy]ethyl-rapamycin; tacrolimus and dexamethasone.

The drug can be also included in micro-depot areas of a stent. Different drugs can be used with the same stent. For example, paclitaxel can be loaded in the micro-depot areas, everolimus in the drug-reservoir layer, and dexamethasone in the finishing coat layer.

In accordance with another embodiment, the drug, such as estradiol, can be incorporated into a polymeric reservoir layer or the optional finishing coat layer in the form of particles of micron to sub-micron size. For example, the particles can have a diameter between about 0.5 and 4.0 μm. The drug can be encapsulated into the particles, followed by suspending the particles in the polymer solution. The suspension can be then applied to the stent. By way of example, the mass ratio between micro- or nanoparticles and the polymer in the suspension can be within a range of between about 1:5 and 1:10.

The particles can be defined by spherical outer shells made of an encapsulating polymer which include an inside space filled with the drug. When the stent is in contact with body fluids, the polymer forming the outer shell of the particles can hydrolyze and degrade thus releasing the drug. The particles can be made by emulsion method according to techniques known to those having ordinary skill in the art. Examples of suitable encapsulating polymers include poly(glycolic acid) (PGA), poly(D-lactic acid)(PDLA), poly(L-lactic acid) (PLLA), poly(butylene terephtalate-co-ethylene glycol) (PBT-PEG), and mixtures thereof.

Figure 1B:
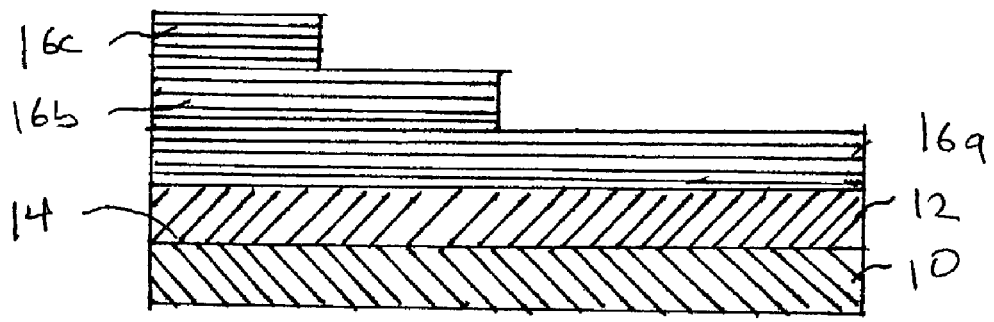
Figure 1C:
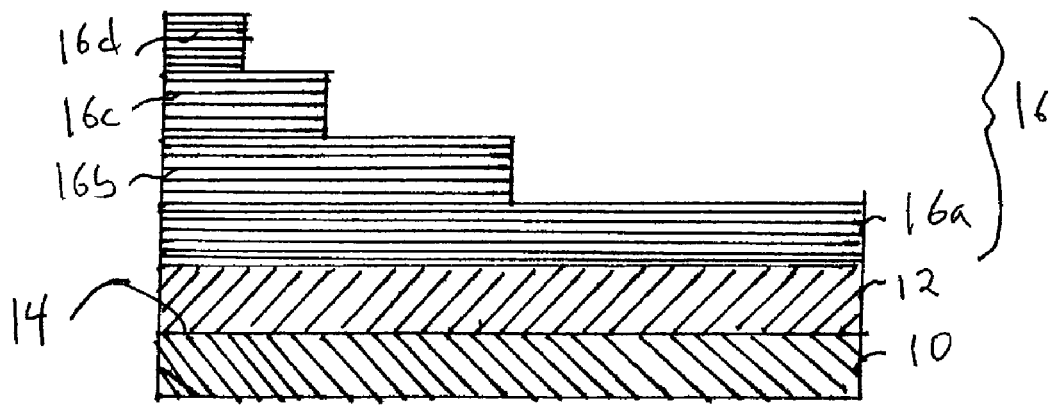

In accordance with one embodiment of the invention, the reservoir layer can have a variable thickness along at least a segment of the length of the stent. Referring to FIGS. 1A, 1B, and 1C, there is illustrated a portion of the length of a stent substrate 10. An optional primer layer 12 can be deposited on an outer surface 14 of the substrate 10. The primer layer 12 should be free from any therapeutic substances so as to serve as an adhesive tie layer between the surface 14 of the stent, which is typically made from a metallic material such as stainless steel, and a reservoir layer 16. A first layer 16a for the reservoir layer 16 can be deposited on the primer layer 12 followed by masking a portion of the first layer 16a. The masking can be accomplished by any variety of methods known to one having ordinary skill in the art, such as by a plastic tape. By way of example, at least 50% of the length of the first layer 16a can be covered, followed by the deposition of a second layer 16b. The steps of masking and deposition can be repeated to form any suitable number of sub-layers. FIGS. 1B and 1C illustrate additionally masking and deposition steps for forming third and forth layers 16c and 16d. Each sub layer 16a-16d can include the same drug, a different drug, or a different combination of drugs. In one embodiment, the more water soluble drugs can be incorporated in the more deeper areas of reservoir layer 16 (e.g., layers 16a or 16b) and the less water soluble drugs can be in the shallower regions (e.g., 16c or 16d).

Figure 2:
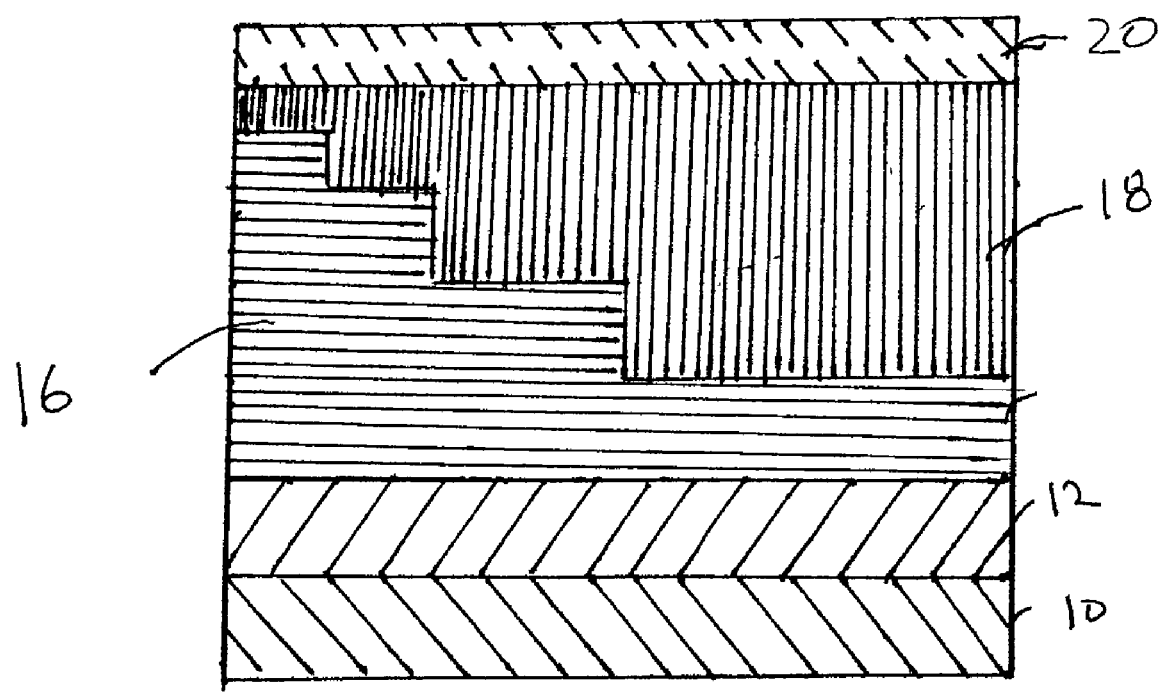
FIG. 2 illustrates a cross-section of one embodiment of a stent coating of the present invention.

When the last desired sub-layer of the reservoir layer 16 has been formed, the masking material is removed and discarded, and a topcoat layer 18 or a finishing coat layer 20 can be deposited on reservoir layer 16. If a topcoat layer is used, the finishing coat layer can be applied over the topcoat layer. FIG. 2 illustrates a cross sectional view of a segment of the end product of the coating configuration. As illustrated in FIG. 2, the reservoir layer 16 has a variable thickness along the longitudinal length of at least a segment of the stent, which provides for a concentration gradient for the drug in the reservoir layer 16. The thicker portions of the reservoir layer 16 will have a higher quantity of a drug or combination of drugs that the thinner portions. The thickness of the reservoir layer 16 increases from one region of the stent in a step-wise configuration towards a second region of the substrate 10. The addition of the topcoat layer 18 or a finishing coating layer 20, however, produces a planar topography for the finished product.

In accordance with one embodiment of the invention, a stent coating that develops cracks immediately upon expansion of the stent can be fabricated. This coating can be used if a high rate of release of the drug is desired. The cracks which typically develop across the entire coating may help to achieve such high rate of release by providing a channel through which the drug would easily and quickly diffuse from the drug-polymer layer through the topcoat membrane.

The coatings and methods of the present invention have been described in conjunction with a stent. The stent can be a balloon-expandable or self-expandable stent, or can include micro-depot areas to contain drugs. The use of the coating, however, is not limited to stents and the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation).

The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Various embodiments of the present invention can be further illustrated by the following examples.

EXAMPLE 1

A first composition can be prepared by mixing the following components:

(a) between about 1.0 mass % and about 15 mass %, for example, about 2.0 mass % of EVAL; and (b) the balance, DMAC solvent.

The first composition can be sprayed on the surface of a bare 13 mm TETRA stent (available from Guidant Corporation). The spray can have a 0.014 fan nozzle maintained at about 60° C. with a feed pressure of about 0.2 atm (about 3 psi) and an atomization pressure of about 1.3 atm (about 20 psi). Between about 40 μg and 100 μg, for example, about 70 μg of the wet coating can be applied. The composition can be baked at about 140° C. for about 2 hours, yielding a dry primer layer.

A second composition can be prepared by mixing the following components:

(c) between about 1.0 mass % and about 15 mass %, for example, about 2.0 mass % of EVAL;

(d) between about 0.5 mass % and about 2.0 mass %, for example, about 1.0 mass % of estradiol; and (e) the balance, DMAC solvent.

The second composition can be applied onto the dried primer layer to form a drug-polymer or reservoir layer, using the same spraying technique and equipment used for applying the primer layer. Between about 300 μg and 500 μg of the wet coating can be applied, followed by drying by baking the stent. The dry drug-polymer layer can contain between about 30 and 70 mass % of the drug, for example, between about 34 and 63 mass %, corresponding to the drug/polymer ration in the dry reservoir layer between about 1:2.3 and about 1:0.4, for example, between about 1:1.9 and 1:0.6.

A third composition can be prepared by mixing the following components:

(f) between about 1.0 mass % and about 15 mass %, for example, about 2.0 mass % of PBMA; and (g) the balance, a mixture of solvents including xylene, FLUX REMOVER AMS ("FLUX REMOVER") and acetone in a ratio of about 25:19:5 by mass.

The third composition can be applied onto the dried drug-polymer layer, to form a topcoat layer. Between about 150 μg and 300 μg, for example, about 200 μg of the wet coating can be applied, followed by drying.

A fourth composition can be prepared by mixing the following components:

(h) between about 1.0 mass % and about 15 mass %, for example, about 1.0 mass % of PBMA;

(i) between about 0.5 mass % and about 2.0 mass %, for example, about 1 mass % of estradiol; and (j) the balance, a mixture of solvents including xylene, FLUX REMOVER, and acetone in a ratio of about 25:19:5 by mass.

The fourth composition can be applied onto the dried topcoat layer, to form a finishing coat layer. Between about 100 μg and 175 μg, for example, about 100 μg of the wet coating can be applied, followed by drying. The dry finishing coat layer can contain between about 33 and 70 mass % of the drug, corresponding to the drug/polymer ration in the finishing coat layer between about 1:2 and about 1:0.4.

Figure 3:
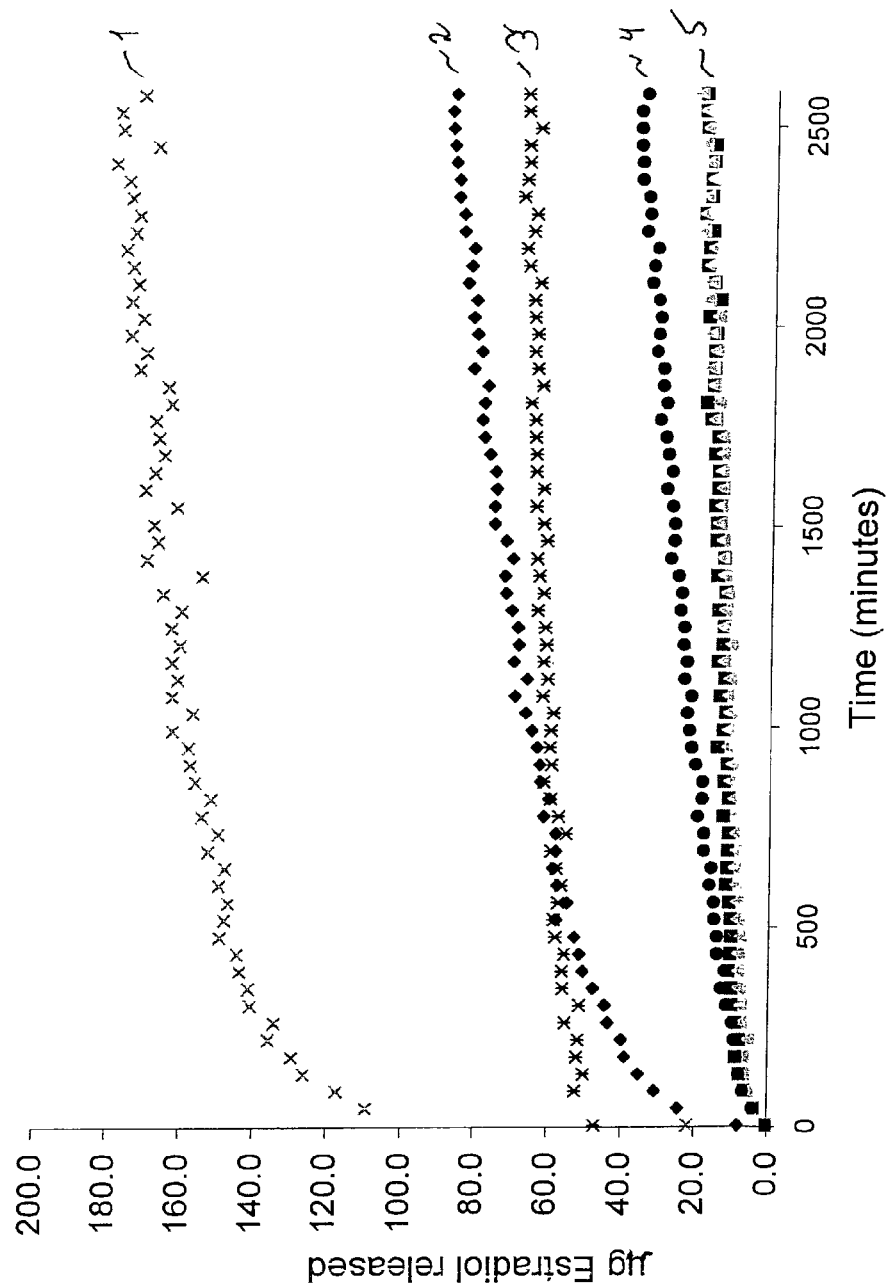
FIG. 3 is a chart showing rates of release of a drug from various stents coated in accordance with an embodiment of the present invention.

The rate of release of estradiol from various stents coated according to the procedure of Example 1 was measured by using a standard technique known to those having ordinary skill in the art. FIG. 3 shows the rates of release of estradiol for 5 stents (curves 1-5) coated with various compositions within ranges described in Example 1. As shown by FIG. 3, for every one of five stents there was a "burst" in the release rate of estradiol at the initial stage. During later stages, the rate of release was close to linear.

EXAMPLE 2

A primer layer can be formed as described in Example 1. A first composition can be prepared by mixing the following components:

(a) between about 0.1 mass % and about 15 mass %, for example, about 1.0 mass % of EVAL;

(b) between about 0.5 mass % and about 2.0 mass %, for example, about 1.0 mass % of estradiol; and (c) the balance, DMAC solvent.

About 250 μg of the wet composition can be applied onto the dried primer layer, followed by drying, to form a drug-polymer layer.

A second composition can be prepared by mixing the following components:

(d) between about 0.1 mass % and about 15 mass %, for example, about 2.0 mass % of PBMA; and (e) the balance, a solvent mixture including cyclohexanone and FLUX REMOVER in a ratio of about 30:19 by mass.

About 300 μg of the wet composition can be applied onto the drug-polymer layer, followed by drying, to form the topcoat layer.

A third composition can be prepared by mixing the following components:

(f) between about 1.0 mass % and about 15 mass %, for example, about 1.5 mass % of PBMA;

(g) between about 0.5 mass % and about 2.0 mass %, for example, about 1 mass % of estradiol; and (h) the balance, a mixture of solvents including acetone, cyclohexanone and FLUX REMOVER, in a ratio of about 16:12:11 by mass.

About 75 μg of the wet composition can be applied onto the dried topcoat layer, followed by drying, to form a finishing coat layer.

EXAMPLE 3

A drug-polymer layer disposed on top of an optional primer layer can be formed as described in Example 2. A first composition can be prepared by mixing the following components:

(a) between about 0.1 mass % and about 15 mass %, for example, about 2.0 mass % of KYNAR; and (b) the balance, a solvent mixture including acetone, cyclohexanone and FLUX REMOVER in a ratio of about 50:25:23 by mass.

About 300 μg of the wet composition can be applied onto the drug-polymer layer, followed by drying.

A second composition can be prepared by mixing the following components:

(c) between about 0.5 mass % and about 15 mass %, for example, about 1.0 mass % of KYNAR;

(d) between about 0.05 mass % and about 2.0 mass %, for example, about 1.0 mass % of estradiol; and (e) the balance, a mixture of solvents including acetone, cyclohexanone and FLUX REMOVER, in a ratio of about 50:250:23 by mass.

Between about 100 μg and 175 μg of the wet coating can be applied, followed by drying. The dry finishing coat layer can contain between about 33 and 56 mass % of the drug, corresponding to the drug/polymer ration in the finishing coat layer between about 1:2 and about 1:0.8.

EXAMPLE 4

A primer layer can be formed as described in Example 1. A first composition can be prepared by mixing the following components:
(a) between about 0.1 mass % and about 15 mass %, for example, about 2.0 mass % of EVAL;
(b) between about 0.5 mass % and about 2.0 mass %, for example, about 1.0 mass % of estradiol; and
(c) the balance, a solvent mixture, the mixture including DMAC and ethanol (EtOH) in a ratio of about 57:40 by mass.

About 300 μg of the wet composition can be applied onto the dried primer layer, followed by drying to form a first sub-layer of a drug-polymer layer.

A second composition, a suspension, can be prepared by mixing the following components:
(d) between about 0.5 mass % and about 15 mass %, for example, about 1.0 mass % of PBMA;
(e) between about 0.5 mass % and about 2.0 mass %, for example, about 2.0 mass % of drug-loaded particles (DLP), the DLP comprising estradiol incorporated in a shell made of PLLA; and
(f) the balance, a mixture of solvents including ethanol, FLUX REMOVER, and acetone, in a ratio of about 40:37:20 by mass.

About 300 μg of the suspension can be applied onto the first sub-layer of the drug-polymer layer to form a second sub-layer of the drug-polymer layer and to complete the formation of the drug-polymer layer.

A third composition can be prepared by mixing the following components:
(g) between about 0.1 mass % and about 15 mass %, for example, about 2.0 mass % of PBMA; and
(h) the balance, a solvent mixture including DMAC and FLUX REMOVER in a ratio of about 30:19 by mass.

About 200 μg of the wet composition can be applied onto the drug-polymer layer, followed by drying, to form the topcoat layer.

A fourth composition can be prepared by mixing the following components:
(i) between about 0.5 mass % and about 15 mass %, for example, about 1.0 mass % of PBMA;
(j) between about 0.5 mass % and about 2.0 mass %, for example, about 1.0 mass % of estradiol; and
(k) the balance, a mixture of solvents including acetone, cyclohexanone and FLUX REMOVER, in a ratio of about 20:15:14 by mass.

About 100 μg of the wet composition can be applied onto the dried topcoat layer followed by drying, to form a finishing coat layer.

EXAMPLE 5

An optional primer layer can be formed as described in Example 1. A first composition can be prepared by mixing the following components:
(a) between about 0.1 mass % and about 15 mass %, for example, about 1.0 mass % of EVAL;
(b) between about 0.5 mass % and about 2.0 mass %, for example, about 1.0 mass % of estradiol; and
(c) the balance, DMAC solvent.

About 250 μg of the wet first composition can be applied onto the dried primer layer, followed by drying, to form a first sub-layer of a drug-polymer layer.

A second composition including a suspension can be prepared and applied onto the first sub-layer as described in Example 4, to form a second sub-layer of the drug-polymer layer and to complete the formation of the drug-polymer layer. Following the formation of the drug-polymer layer, a topcoat layer and a finishing coat layer formulations can be prepared and applied to form the topcoat and finishing coat layers, as described in Example 4.

EXAMPLE 6

A first composition can be prepared by mixing the following components:
(a) between about 1.0 mass % and about 15 mass %, for example, about 2.0 mass % of PBMA; and
(b) the balance, cyclohexanone solvent.

About 70 μg of the wet composition can be applied onto the surface of a bare stent to form an optional primer layer.

A second composition can be prepared by mixing the following components:
(c) between about 0.1 mass % and about 15 mass %, for example, about 1.0 mass % of PBMA;
(d) between about 0.5 mass % and about 2.0 mass %, for example, about 1.0 mass % of estradiol; and
(e) the balance, a mixture of solvents, the mixture including xylene, FLUX REMOVER, and acetone in a ratio of about 20:19:10 by mass.

About 75 μg of the wet second composition can be applied onto the dried primer layer, followed by drying, to form a first sub-layer of a drug-polymer layer. Following formation of the first sub-layer of the drug-polymer layer, a portion of the first sub-layer can be masked (about 50% of the length of the first sub-layer can be masked).

A third composition can be prepared by mixing the following components:
(f) between about 0.1 mass % and about 15 mass %, for example, about 1.5 mass % of PBMA;
(g) between about 0.5 mass % and about 2.0 mass %, for example, about 1.0 mass % of estradiol; and
(h) the balance, a mixture of solvents, the mixture including xylene, FLUX REMOVER, and acetone in a ratio of about 16:15:8 by mass.

About 75 μg of the wet third composition can be applied onto the dried first sub-layer, followed by drying, to form a second sub-layer of the drug-polymer layer. Following formation of the second sub-layer of the drug-polymer layer, a portion of the second sub-layer can be masked and the steps repeated until the drug-polymer coating has a total of about 300 μg of PBMA and about 200 μg of estradiol.

A final composition can be prepared, containing:
(i) between about 1.0 mass % and about 15 mass %, for example, about 2.0 mass % of PBMA; and
(j) the balance, a mixture of solvents, the mixture including xylene, FLUX REMOVER, and acetone in a ratio of about 20:19:10 by mass.

About 200 μg of the wet final composition can be applied onto the drug-polymer layer, followed by drying, to form the topcoat layer.

EXAMPLE 7

An optional primer layer can be formed as described in Example 1. A first composition can be prepared by mixing the following components:
(a) between about 0.1 mass % and about 15 mass %, for example, about 1.5 mass % of PBMA;

(b) between about 0.5 mass % and about 2.0 mass %, for example, about 1.0 mass % of estradiol; and (c) the balance, a mixture of solvents, the mixture including xylene, FLUX REMOVER, and acetone in a ratio of about 16:15:8 by mass.

About 75 µg of the wet first composition can be applied onto the dried primer layer, followed by drying, to form a first layer of a drug-polymer layer. Following formation of the first layer, a portion of the first layer, for example, about 50% of the length of the first layer, can be masked.

A second composition can be prepared by mixing the following components:

(d) between about 0.1 mass % and about 15 mass %, for example, about 2.0 mass % of PBMA; and (e) the balance, a mixture of solvents, the mixture including xylene, FLUX REMOVER, and acetone in a ratio of about 20:19:10 by mass.

About 200 µg of the wet second composition can be applied onto the first layer, followed by drying, to form a second layer.

A third composition can be prepared by mixing the following components:

(f) between about 0.1 mass % and about 15 mass %, for example, about 1.0 mass % of PBMA;

(g) between about 0.5 mass % and about 2.0 mass %, for example, about 1.0 mass % of estradiol; and (h) the balance, a mixture of solvents, the mixture including xylene, FLUX REMOVER, and acetone in a ratio of about 20:19:10 by mass.

About 75 µg of the wet third composition can be applied to the stent, followed by drying, to form a third layer. Following formation of the third layer, a portion of the third layer, for example, about 50% of the length of the third layer can be masked.

A fourth composition can be prepared by mixing the following components:

(i) between about 0.1 mass % and about 15 mass %, for example, about 2.0 mass % of PBMA; and (j) the balance, a mixture of solvents, the mixture including xylene, FLUX REMOVER, and acetone in a ratio of about 20:19:10 by mass.

About 100 µg of the wet fourth composition can be applied to the stent, followed by drying to form a fourth layer.

A fifth composition can be prepared by mixing the following components:

(k) between about 0.1 mass % and about 15 mass %, for example, about 1.0 mass % of PBMA;

(l) between about 0.5 mass % and about 2.0 mass %, for example, about 1.0 mass % of estradiol; and (m) the balance, a mixture of solvents including xylene, FLUX REMOVER, and acetone in a ratio of about 20:19:10 by mass.

About 75 µg of the wet fifth composition can be applied onto the stent, followed by drying, to form a fifth layer.

A sixth composition can be prepared by mixing the following components:

(n) between about 0.1 mass % and about 15 mass %, for example, about 2.0 mass % of PBMA; and (o) the balance, a mixture of solvents, xylene, FLUX REMOVER, and acetone in a ratio of about 20:19:10 by mass.

About 200 µg of the wet sixth composition can be applied, followed by drying, to form a topcoat layer.

EXAMPLE 8

A first composition was prepared by mixing the following components:

(a) about 3.0 mass % of EVAL;

(b) about 25 mass % of ethanol; and (c) the balance, DMAC solvent.

The first composition was applied onto the stent to form a primer layer as described in Example 1. The primer layer had solids of about 40 µg.

A second composition was prepared by mixing the following components:

(d) about 2.0 mass % of EVAL;

(e) about 1.0 mass % of EVEROLIMUS;

(f) about 25 mass % of pentane; and (g) the balance, DMAC solvent.

The second composition was applied onto the dried primer layer to form a drug-polymer layer as described in Example 1. The drug-polymer layer was dried for about 1 hour at a temperature of about 80° C., to form the dry reservoir layer having solids of about 834 µg.

A third composition was prepared by mixing the following components:

(h) about 4.0 mass % of EVAL;

(i) about 20 mass % of pentane; and (j) the balance, DMAC solvent.

The third composition was onto the dried drug-polymer layer, to form a topcoat layer, as described in Example 1. The drug-polymer layer was dried for about 1 hour at a temperature of about 80° C., to form the dry reservoir layer having solids of about 100 µg.

Figure 4:
FIG. 4 is a microphotograph showing cracks in a stent coating according to one embodiment of the present invention.

The stent coated as described in Example 8 was expanded. Immediately upon the expansion, the cracks developed across the entire coating, as shown by the microphotograph presented in FIG. 4.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent having a coating, the coating comprising a first region including a thermoplastic polyacrylate material and a therapeutic substance and a second region free from any therapeutic substances disposed on the surface of the stent and beneath the first region, wherein the second region comprises a polymer selected from the group consisting of a fluorinated polymers, poly(ethylene-co-vinyl alcohol), polydioxanone, poly (glycolic acid-co-trimethylene carbonate), polyphosphoester, polyphosphoester urethane, polycyanoacrylates, poly(trimethylene carbonate), poly (iminocarbonate), co-poly(ether-esters), polyalkylene oxalates, polyurethanes, silicones, polyisobutylene, ethylene-alphaolefin copolymers, vinyl halide polymers and copolymers, polyvinyl ethers, polyvinylidene chloride, polyacrylonitrile, polyvinyl ketones, polyvinyl aromatics, ethylene-methyl methacrylate copolymers, acrylonitrile-styrene copolymers, ABS resins, polyamides, alkyd resins, polyoxymethylenes, polyimides, polyethers, epoxy resins, polyurethanes, rayon, rayon-triacetate, fibrin, fibrinogen, cellulose, collagen, hyaluronic acid, cellulose acetate, cellulose butyrate, cellulose acetate butyrate, cellophane, cellulose nitrate, cellulose propionate, cellulose ethers, and carboxymethyl cellulose.

2. The stent of claim 1, wherein the thermoplastic polyacrylate material comprises oligomers, pre-polymers, homopolymers, copolymers, or terpolymers of alkylacrylates or alkylmethacrylates.

3. The stent of claim 2, wherein the alkyls in the alkylacrylates or alkylmethacrylates are $C_1$-$C_{12}$ straight-chained or branched alkyls.

4. A stent having a coating, the coating comprising a first region including a thermoplastic polyacrylate material and a therapeutic substance and a second region free from any therapeutic substances disposed on the surface of the stent and beneath the first region,
   wherein the polyacrylate material comprises poly(butyl methacrylate), and
   wherein the second region comprises a polymer selected from the group consisting of fluorinated polymers, poly(ethylene-co-vinyl alcohol), polydioxanone, poly(glycolic acid-co-trimethylene carbonate), polyphosphoester, polyphosphoester urethane, polycyanoacrylates, poly(trimethylene carbonate), poly(iminocarbonate), co-poly(ether-esters), polyalkylene oxalates, polmurethanes, silicones, polyisobutylene, ethylene-alphaolefin copolymers, vinyl halide polymers and copolymers, polyvinyl ethers, polyvinylidene chloride, polyacrylonitrile, polyvinyl ketones, polyvinyl aromatics, ethylene-methyl methacrylate copolymers, acrylonitrile-styrene copolymers, ABS resins, polyamides, alkyd resins, polyoxymethylenes, polyimides, polyethers, epoxy resins, polyurethanes, rayon, ravon-triacetate, fibrin, fibrinogen, cellulose, collagen, hyaluronic acid, cellulose acetate, cellulose butyrate, cellulose acetate butyrate, cellophane, cellulose nitrate, cellulose propionate, cellulose ethers, and carboxymethyl cellulose.

5. The stent of claim 1, wherein the second region includes a non-acrylate polymer.

6. A stent having a coating, the coating comprising a first region including a thermoplastic polyacrylate material and a therapeutic substance and a second region free from any therapeutic substances disposed on the surface of the stent and beneath the first region, wherein the second region includes an ethylene vinyl alcohol copolymer.

7. The stent of claim 1, wherein the second region further includes a thermoplastic polyacrylate material.

8. The stent of claim 6, wherein the polyacrylate material comprises poly(butyl methacrylate).

9. The stent of claim 1, wherein the first region further includes a non-acrylate polymer blended with the thermoplastic polyacrylate material.

10. The stent of claim 1, additionally including a third region disposed over the first region, the third region including a thermoplastic polyacrylate material and optionally a therapeutic substance.

11. The stent of claim 1, wherein the first region has a variable thickness along at least a segment of the length of the stent.

12. The stent of claim 1, wherein the concentration of the substance is greater in a first area of the first region than in a second area of the first region.

13. A stent comprising a coating, wherein the coating comprises a first, second, and third layers disposed over one another wherein the second layer includes a thermoplastic polyacrylate material,
   wherein at least one of the layers includes a therapeutic substance,
   wherein the first layer is disposed on the outer surface of the stent, and
   wherein the third layer comprises a polymer selected from the group consisting of fluorinated polymers, poly(ethylene-co-vinyl alcohol), polydioxanone, poly(glycolic acid-co-trimethylene carbonate), polyphosphoester, polyphosphoester urethane, polycyanoacrylates, poly(trimethylene carbonate), poly(iminocarbonate), co-poly(ether-esters), polyalkylene oxalates, polyurethanes, silicones, polyisobutylene, ethylene-alphaolefin copolymers, vinyl halide polymers and copolymers, polyvinyl ethers, polyvinylidene chloride, polyacrylonitrile, polyvinyl ketones, polyvinyl aromatics, ethylene-methyl methacrylate copolymers, acrylonitrile-styrene copolymers, ABS resins, polyamides, alkyd resins, polyoxymethylenes, polyimides, polyethers, epoxy resins, polyurethanes, rayon, rayon-triacetate, fibrin, fibrinogen, cellulose, collagen, hyaluronic acid, cellulose acetate, cellulose butyrate, cellulose acetate butyrate, cellophane, cellulose nitrate, cellulose propionate, cellulose ethers, and carboxymethyl cellulose.

14. The stent of claim 13, wherein the therapeutic substance is contained in the second layer and optionally the third layer but not the first layer.

15. The stent of claim 13, wherein the first layer and the third layer include the therapeutic substance but not the second layer.

16. The stent of claim 15, wherein the first layer is disposed on a primer layer, the primer layer being disposed on the surface of the stent.

17. The stent of claim 13, wherein the first layer includes a polyacrylate material, and wherein at least one of the layers is free from any therapeutic substances.

18. The stent of claim 17, wherein the first layer is disposed on the outer surface of the stent and is free from any therapeutic substances.

* * * * *